US00PP20632P2

(12) United States Plant Patent
Koning

(10) Patent No.: US PP20,632 P2
(45) Date of Patent: Jan. 5, 2010

(54) LAVENDER PLANT NAMED 'SANNE'

(50) Latin Name: *Lavandula stoechas*
Varietal Denomination: Sanne

(75) Inventor: Lammert Koning, Nuis (NL)

(73) Assignee: Koning Smit Holding B.V., Curacao (NL)

( * ) Notice: Subject to any disclaimer, the term of this patent is extended or adjusted under 35 U.S.C. 154(b) by 0 days.

(21) Appl. No.: 12/228,289

(22) Filed: Aug. 11, 2008

(51) Int. Cl.
*A01H 5/00* (2006.01)

(52) U.S. Cl. ..... Plt./445

(58) Field of Classification Search ..... Plt./445, Plt./226
See application file for complete search history.

(56) References Cited

OTHER PUBLICATIONS

Upov-rom GTITM Plant Variety Database 2009/02, GTI Jouve Retrieval Software, Citation for Lavandula 'Sanne', one page.*

* cited by examiner

*Primary Examiner*—June Hwu
(74) *Attorney, Agent, or Firm*—C. A. Whealy

(57) ABSTRACT

A new and distinct cultivar of Lavender plant named 'Sanne', characterized by its compact, upright and somewhat outwardly spreading plant habit; freely branching growth habit; durable green-colored leaves; freely flowering habit; large purple violet-colored flowers arranged in compact verticillasters on crowded spikes and good garden performance.

2 Drawing Sheets

Botanical designation: *Lavandula stoechas.*
Cultivar denomination: 'Sanne'.

BACKGROUND OF THE INVENTION

The present invention relates to a new and distinct cultivar of Lavender plant, botanically known as *Lavandula stoechas,* and hereinafter referred to by the name 'Sanne'.

The new Lavender plant is a product of a planned breeding program conducted by the Inventor in Nuis, The Netherlands. The objective of the breeding program was to develop new strong Lavender cultivars with attractive plant form and flower coloration.

The new Lavender plant originated from a cross-pollination made by the Inventor in July, 2004 of a proprietary selection of *Lavandula stoechas* identified as code number SLA 125, not patented, as the female, or seed, parent with a proprietary selection of *Lavandula stoechas* identified as code number SLA 231, not patented, as the male, or pollen, parent. The new Lavender plant was discovered and selected by the Inventor in August, 2005 as a single flowering plant within the progeny of the stated cross-pollination in a controlled outdoor nursery environment in Nuis, The Netherlands.

Asexual reproduction of the new Lavender by terminal cuttings in a controlled greenhouse environment in Sappemeer, The Netherlands since November, 2005, has shown that the unique features of this new Lavender plant are stable and reproduced true to type in successive generations.

SUMMARY OF THE INVENTION

Plants of the new Lavender have not been observed under all possible environmental conditions. The phenotype may vary somewhat with variations in environment such as temperature and light intensity, without, however, any variance in genotype.

The following traits have been repeatedly observed and are determined to be the unique characteristics of the new Lavender plant. These characteristics in combination distinguish 'Sanne' as a new and distinct cultivar of Lavender:

1. Compact, upright and somewhat outwardly spreading plant habit.
2. Freely branching growth habit.
3. Durable green-colored leaves.
4. Freely flowering habit.
5. Large purple violet-colored flowers arranged in compact verticillasters on crowded spikes.
6. Good garden performance.

Plants of the new Lavender differ from plants of the female parent selection in the following characteristics:

1. Plants of the new Lavender are more compact than plants of the female parent selection.
2. Plants of the new Lavender are more freely branching than plants of the female parent selection.
3. Plants of the new Lavender are more freely flowering than plants of the female parent selection.

Plants of the new Lavender differ from plants of the male parent selection in the following characteristics:

1. Plants of the new Lavender have stronger peduncles than plants of the male parent selection.
2. Plants of the new Lavender and the male parent selection differ in flower color as flower color plants of the male parent selection is less intense.

Plants of the new Lavender can be compared to plants of *Lavandula stoechas* 'Anouk', disclosed in U.S. Plant Pat. No. 16,685. Plants of the new Lavender differ from plants of 'Anouk' in the following characteristics:

1. Plants of the new Lavender are more compact than plants of 'Anouk'.
2. Plants of the new Lavender have shorter peduncles than plants of 'Anouk'.

Plants of the new Lavender can also be compared to plants of *Lavandula stoechas* 'Alexandra', not patented. Plants of the new Lavender differ from plants of 'Alexandra' in the following characteristics:

1. Plants of the new Lavender have shorter terminal bracts than plants of 'Alexandra'.
2. Plants of the new Lavender have sturdier stems than plants of 'Alexandra'.

BRIEF DESCRIPTION OF THE PHOTOGRAPHS

The accompanying photographs illustrate the overall appearance of the new Lavender plant. These photographs show the colors as true as it is reasonably possible to obtain in colored reproductions of this type. Colors in the photographs may differ slightly from the color values cited in the detailed botanical description which accurately describe the colors of the new Lavender.

The photograph on the first sheet comprises a side perspective view of a typical flowering plant of 'Sanne' grown in a container.

The photograph at the top of the second sheet is a close-up view of a typical inflorescence of 'Sanne'.

The photograph at the bottom of the second sheet is a close-up view of the upper surface of a typical leaf of 'Sanne'.

DETAILED BOTANICAL DESCRIPTION

In the following description, color references are made to The Royal Horticultural Society Colour Chart, 2001 Edition, except where general terms of ordinary dictionary significance are used. The aforementioned photographs, following observations and measurements describe plants grown in 14-cm containers in Boskoop, The Netherlands during the spring in an outdoor nursery and under conditions and practices which approximate those generally used in commercial Lavender production. Measurements and numerical values represent averages for typical flowering plants. Plants were pinched once and were one year old when the photographs and description were taken. During the production of the plants, day temperatures ranged from 4° C. to 20° C. and night temperatures ranged from 0° C. to 14° C.

Botanical classification: *Lavandula stoechas* 'Sanne'.

Parentage:

*Female, or seed, parent.*—Proprietary selection of *Lavandula stoechas* identified as code number SLA 125, not patented.

*Male, or pollen, parent.*—Proprietary selection of *Lavandula stoechas* identified as code number SLA 231, not patented.

Propagation:

*Type.*—Terminal vegetative cuttings.

*Time to initiate roots, summer.*—About two weeks at 14° C. to 25° C.

*Time to initiate roots, winter.*—About three weeks at 14° C. to 25° C.

*Time to produce a rooted young plant, summer.*—About eight weeks at 14° C. to 25° C.

*Time to produce a rooted young plant, winter.*—About ten weeks at 14° C. to 25° C.

*Root description.*—Fine, fibrous; white in color.

*Rooting habit.*—Freely branching; dense.

Plant description:

*Form.*—Herbaceous perennial subshrub. Compact, upright and outwardly spreading plant habit; broad inverted triangle.

*Growth habit.*—Moderately vigorous.

*Branching habit.*—Freely branching habit, about 39 lateral branches.

*Plant height.*—About 24.7 cm.

*Plant width.*—About 28.5 cm.

*Lateral branch description.*—Length: About 10.3 cm. Diameter: About 2 mm. Internode length: About 1.8 cm. Strength: Strong. Aspect: Mostly upright to outward. Texture: Pubescent. Color: Close to 144A; pubescence, close to 157C to 157D.

*Foliage description.*—Arrangement: Opposite, simple; sessile. Length: About 2.9 cm. Width: About 4 mm. Shape: Lanceolate. Apex: Acute. Base: Cuneate. Margin: Entire. Texture, upper and lower surfaces: Densely pubescent. Fragrance: Very aromatic, pungent. Venation pattern: Pinnate. Color: Developing leaves, upper surface: Close to 137B. Developing leaves, lower surface: Close to 138A. Fully expanded leaves, upper surface: Between 137A and 139A; venation, close to 148C; pubescence, close to 157C to 157D. Fully expanded leaves, lower surface: Close to 137B; venation, close to 144B; pubescence, close to 157C to 157D.

Flower description:

*Flower arrangement and shape.*—Single sessile flowers arranged in compact verticillasters on crowded spikes. Freely flowering, about 100 open flowers and flower buds per spike; flowers salverform with a two-lobed upper lip and a three-lobed lower lip.

*Natural flowering season.*—Long flowering period; continuous throughout the summer in The Netherlands.

*Flower longevity on the plant.*—Individual inflorescences last about ten days on the plant. Flowers not persistent.

*Fragrance.*—None detected.

*Flower buds.*—Length: About 3.5 mm. Diameter: About 1.5 mm. Shape: Obovate. Color: Close to 191C.

*Inflorescence size.*—Height: About 3.7 cm. Diameter, apex: About 1.7 cm. Diameter, base: About 1.2 cm.

*Flowers.*—Diameter: About 3 mm. Depth (height): About 7 mm.

*Petals.*—Lip length: About 7 mm. Lip width: About 1.5 mm. Lip shape: Roughly spatulate. Lip: Rounded; emarginate. Lip margin: Entire. Lip texture, upper and lower surfaces: Smooth, glabrous. Lip color: When opening, upper and lower surfaces: Slightly darker than N92A; tube, close to N81A to N81B. Fully opened, upper and lower surfaces: Slightly darker than N92A; tube, close to N81A to N81B. With development, color becoming closer to N186B.

*Terminal flower bracts.*—Quantity/arrangement: About twelve at inflorescence apex. Length, outer bracts: About 2 cm. Width, outer bracts: About 8 mm. Length, inner bracts: About 9 mm. Width, inner bracts: About 4 mm. Shape: Obovate. Apex: Obtuse. Base: Cuneate. Margin: Entire. Texture, upper and lower surfaces: Smooth, glabrous. Color, outer bracts, upper and lower surfaces: Close to N81A to N81B. Color, inner bracts, upper and lower surfaces: Close to N82C.

*Flower bracts.*—Arrangement: Each whorl of flowers subtended by a flower bract. Length: About 8 mm. Width: About 7 mm. Shape: Broadly rhomboidal. Apex: Broadly acute. Base: Cuneate. Margin: Entire.

Texture, upper and lower surfaces: Tomentose. Color, upper and lower surfaces: Close to 71A to 71B; towards the base, close to 145D; venation, close to N186A.

*Sepals.*—Arrangement: Five sepals fused into a campanulate tube. Length: About 5 mm. Width: About 1 mm. Shape: Lanceolate. Apex: Acute. Sepal margin: Entire. Sepal texture, upper and lower surfaces: Pubescent. Color, immature, upper and lower surfaces: Close to 191C. Color, mature, upper and lower surfaces: Close to 138C; pubescence, close to 157C to 157D.

*Peduncles.*—Strength: Strong. Length: About 5.1 cm. Diameter: About 1.5 mm. Aspect: Mostly upright. Texture: Pubescent. Color: Close to 144A; towards the apex, flushed with close to 187A to 187B; pubescence, close to 157C to 157D.

*Pedicels.*—Strength: Moderately strong. Length: About 1 mm. Diameter: About 0.5 mm. Aspect: About 45° from the peduncle. Texture: Pubescent. Color: Close to 145D; pubescence, close to 192D.

*Reproductive organs.*—Stamens: Quantity per flower: Four. Filament length: About 0.5 mm. Anther shape: Reniform. Anther length: About 0.5 mm. Anther color: Close to 165B. Pollen amount: Scarce. Pollen color: Close to 165B to 165C. Pistils: Quantity per flower: One. Pistil length: About 3.5 mm. Stigma shape: Club-shaped. Stigma color: Close to N186A. Style length: About 3 mm. Style color: Close to 155C. Ovary color: Close to 145D.

*Seed/fruit.*—Seed and fruit production has not been observed.

Disease/pest resistance: Plants of the new Lavender have not been noted to be resistant to pathogens and pests common to Lavender.

Garden performance: Plants of the new Lavender have exhibited good tolerance to rain and wind and have been observed to tolerate temperatures from about −15° C. to about 40° C.

It is claimed:

1. A new and distinct Lavender plant named 'Sanne' as illustrated and described.

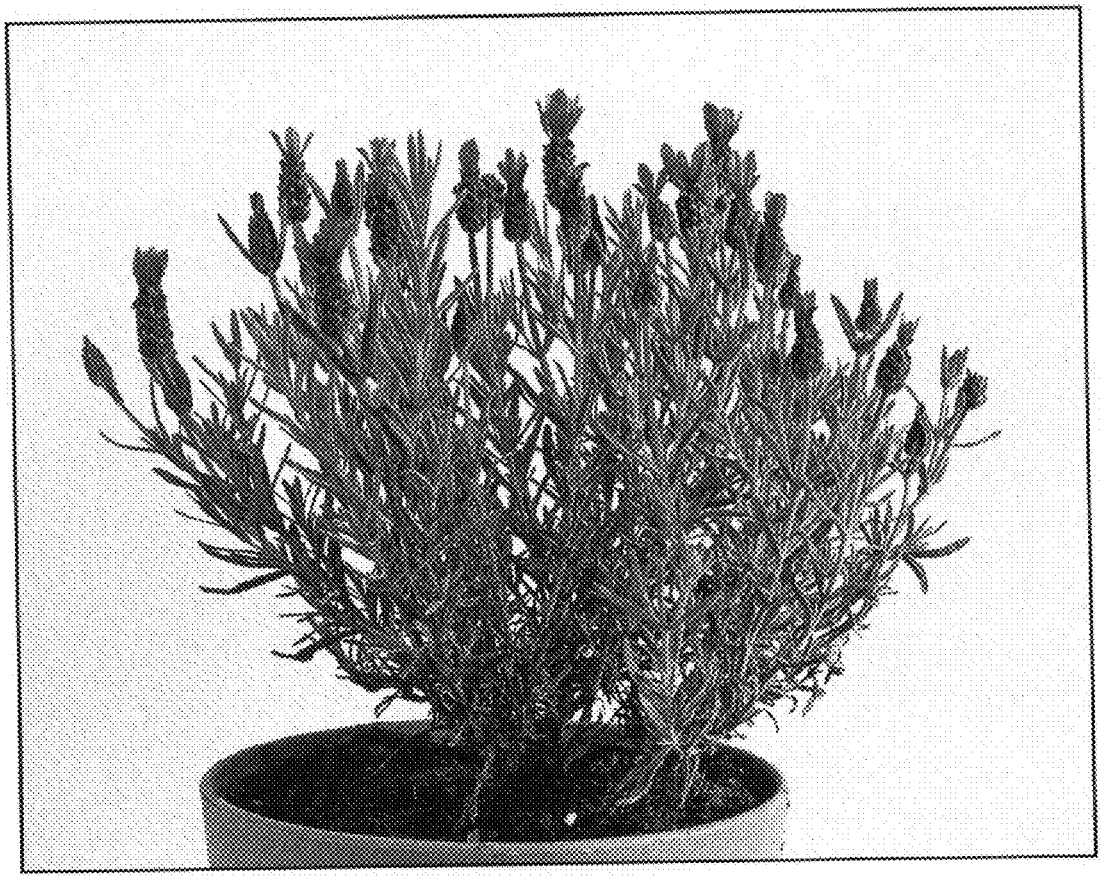

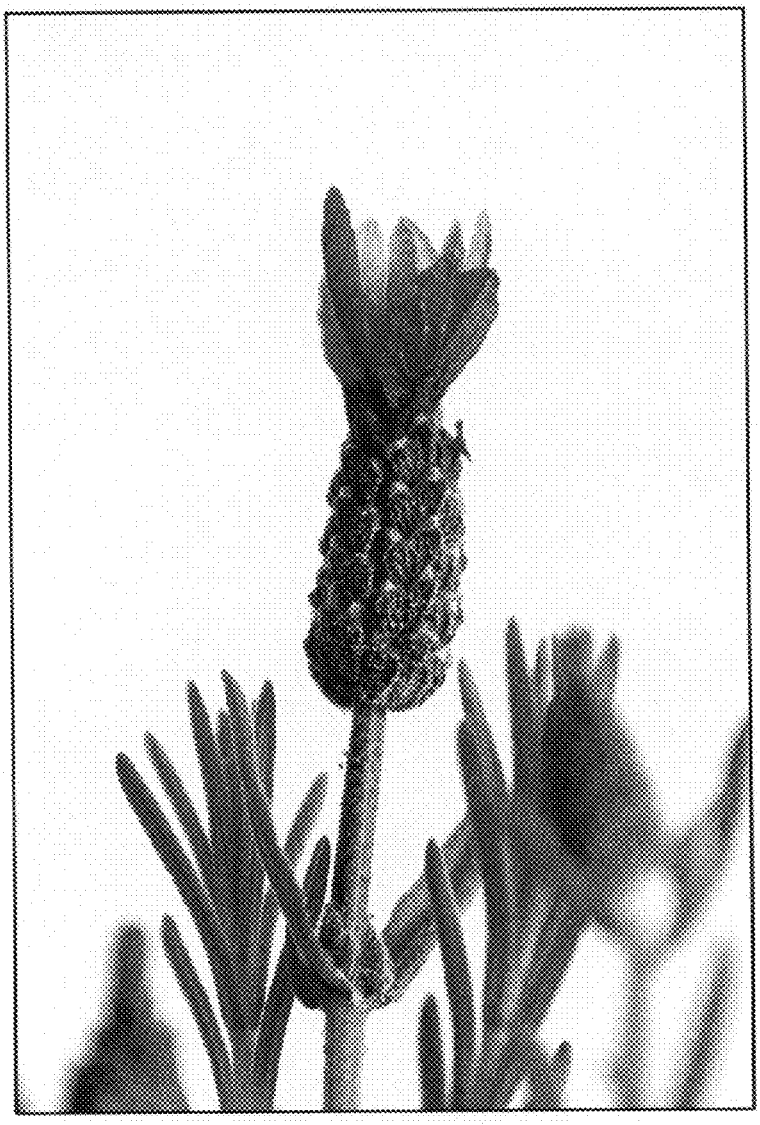
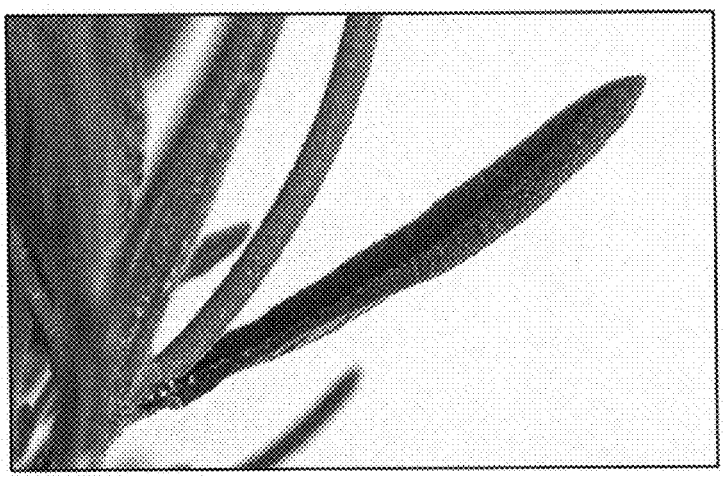

* * * * *